United States Patent [19]

Djordjevich

[11] 3,996,925

[45] Dec. 14, 1976

[54] SYSTEM FOR DETERMINING CHARACTERISTICS OF BLOOD FLOW

[76] Inventor: Ljubomir Djordjevich, 421 Barry Ave., Chicago, Ill. 60657

[22] Filed: May 5, 1975

[21] Appl. No.: 574,471

[52] U.S. Cl. ............... 128/2.05 V; 128/2.05 F; 128/2.1 Z; 235/151.34; 324/65 R; 73/195
[51] Int. Cl.² ............................................. A61B 5/02
[58] Field of Search ............ 128/2.05 V, 2.05 F, 128/2.05 R, 2.1 Z; 324/65 R; 235/151.34; 73/195 E

[56] References Cited

UNITED STATES PATENTS

| | | | |
|---|---|---|---|
| 3,433,935 | 3/1969 | Sherman | 128/2.05 F |
| 3,651,318 | 3/1972 | Czekajewski | 128/2.05 F |
| 3,678,922 | 7/1972 | Phillips et al. | 128/2.05 F |
| 3,835,839 | 9/1974 | Brown | 128/2.05 V |
| 3,835,840 | 9/1974 | Mount | 128/2.05 V |
| 3,874,368 | 4/1975 | Asrican | 128/2.05 V |

OTHER PUBLICATIONS

Ellis et al, "Computerized . . . thermal dilution," JAAMA, vol. 6, No. 2, Mar.–Apr. 1972, pp. 116–121.

*Primary Examiner*—Robert W. Michell
*Assistant Examiner*—Lee S. Cohen
*Attorney, Agent, or Firm*—Carl C. Batz

[57] ABSTRACT

A method and apparatus for determining and displaying without invasion into the vascular system the instantaneous rate of blood flow, the stroke volume during a pulse or cycle, and the cardiac output over a time period. The system involves an arrangement of electronic units through which a signal representing impedance of a section of a living body is passed in a special order and which results in instantaneous and continuous indication of blood flow characteristics through this section.

A principal feature of the system resides in the provision of two electrical channels one of which contains an electronic divider and the other an electronic differentiator both of which channels are connected with a multiplier which multiplies the signal from one channel with the signal from the other channel to produce a signal representative of the rate of instantaneous blood flow through the body section being tested.

21 Claims, 1 Drawing Figure

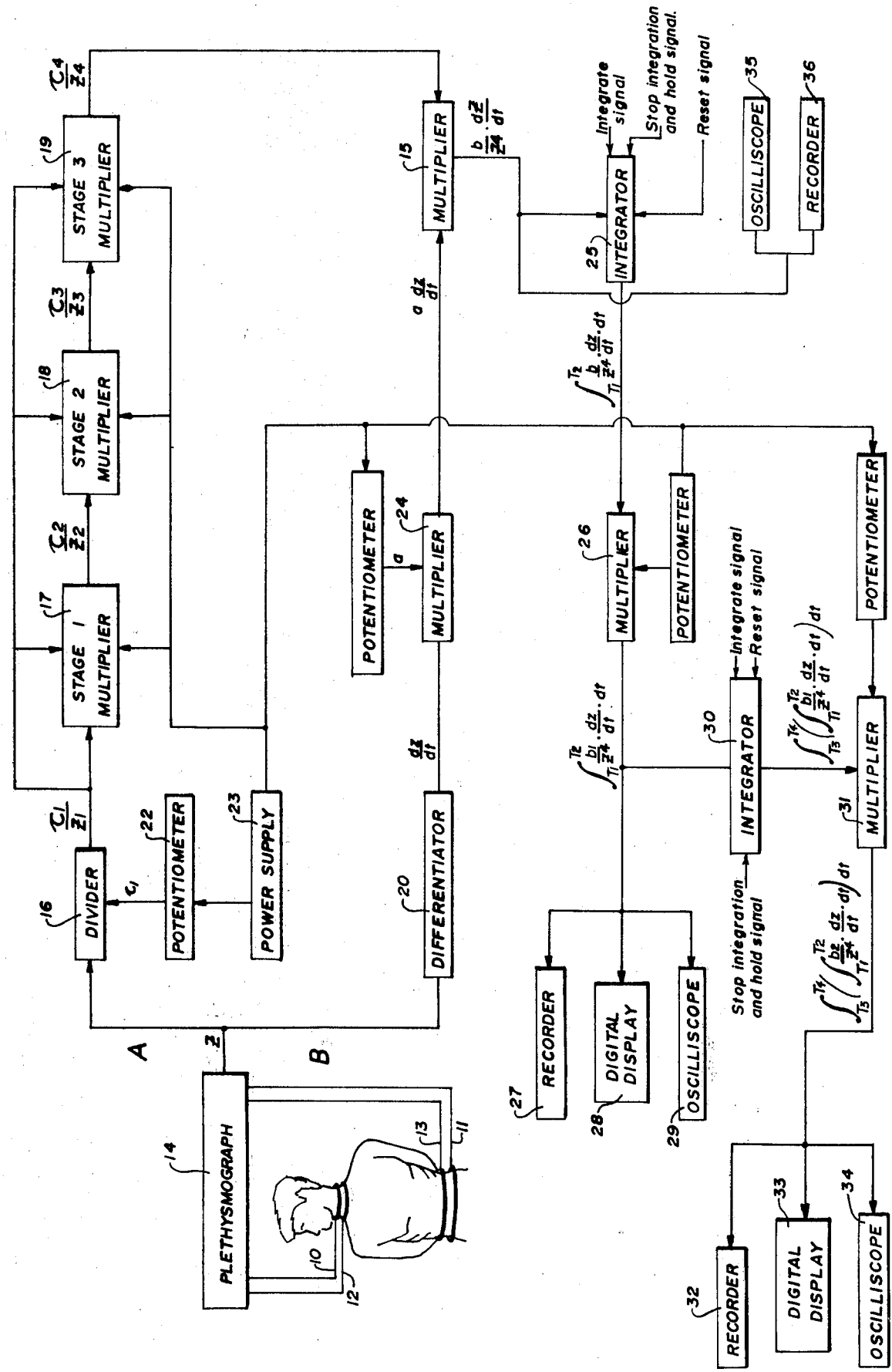

SYSTEM FOR DETERMINING CHARACTERISTICS OF BLOOD FLOW

This invention relates to a process and apparatus for monitoring the flow of blood in a section of a living body without invading the blood vessels of the body. More particularly the invention relates to a process and apparatus in which a signal representing the impedance of the section is produced and passed through electronic units to provide signals which describe parameters of blood flow through this section of the body.

BACKGROUND

Physicians and surgeons have long needed and desired to have a process and apparatus for determining, displaying and recording accurate information concerning instantaneous rates of flow of blood, volume of blood which flows during one pulse (sometimes called stroke volume), the volume of blood which flows during a certain unit of time such as a second, a minute, etc. (sometimes called cardiac output), and other parameters of blood flow, without the necessity for invading the blood vessels.

The body section involved may be the chest which contains the heart and larger arteries, but other body sections such as a leg or an arm may also be utilized.

Because blood, being an electrolyte, is more conductive to electricity than is solid tissue such as muscles, bones or viscera, it has been suggested that the electrical impedance of the section is indicative of the proportion of blood to the tissue in the section. Kubicek et al provided an impedance plethysmograph by which the value of Z, the impedance of the section of the body under test, was determined on a continuing basis. See U.S. Pat. No. 3,340,867 and the article entitled "Applications of the Minnesota Impedance Cardiograph" by Kubicek et al, in publication entitled "Development and Evaluation of an Impedance Cardiographic System to Measure Cardiac Output and Other Cardiac Parameters" by W. G. Kubicek, published by University of Minnesota July 1, 1968-June 30, 1969. Kubicek's apparatus included an outer pair of electrodes one of which was affixed to the patient's neck and the other of which was affixed to the patient's waist and an oscillating current was passed between these outer electrodes. A second pair of electrodes was likewise affixed between the first pair of electrodes for the purpose of measuring the electrical impedance. Although Kubicek's apparatus provided a proper representative value for Z, it provided no means for instantaneous and continuous determination of the rate of flow or volume of flow during one pulse or heartbeat or during any selected period of time.

Mount, in his U.S. Pat. No. 3,835,840, disclosed a plethysmograph apparently of the type disclosed by Kubicek, by which the impedance was determined, and the impedance so determined was fed through a circuit including electronic devices to obtain a signal which was recorded and which was expected to represent the rate of blood flow. But the signal obtained from the apparatus as disclosed by Mount did not represent the rate of blood flow with such accuracy as would be required to make it of substantial value to physicians and surgeons.

Accordingly, I have set about to discover apparatus and processes which do properly yield a signal which accurately represents and indicates the rate of blood flow through a body section on an instantaneous and continuous basis, and which will also indicate stroke volume and the cardiac output.

DESCRIPTION

I propose to take into account the fact that the arteries of a living body are essentially ducts with elastic walls. As the blood pressure varies during the cardiac cycle, the diameters of the arteries may also vary and the flow of blood through the arteries has pulsatile character, which results in periodic accumulation and decumulation of blood in the section of the body subject to test. Based on principles of the mechanics of viscous flow through ducts with elastic walls and the theory of elasticity, I provide the following formula for the instantaneous rate of blood flow:

$$Q = \frac{0.5}{16\pi^2} \cdot \frac{E(k^2-1)}{\mu s R_o^2} \cdot \frac{\rho^3 L^3}{Z^4} \cdot \frac{dz}{dt} \qquad \text{(Formula No. 1)}$$

where
- Q is the instantaneous rate of blood flow in cc per second;
- E is the average Modulus of Elasticity of the arterial walls ($10^6$ dynes per square centimeter is a typical value);
- k is the average ratio of outer to inner radii of the arterial walls (A typical value of k is 1.1);
- $\mu$ is the viscosity of blood (A typical value is 0.03 gm per centimeter per second);
- s is the average speed of propagation of pressure through the arterial walls (A typical value is 1000 centimeters per second);
- $R_o$ is the average radius of the chest of a patient in centimeters measured on the patient;
- $\rho$ is the electrical resistivity of blood (A typical value is 200 ohm-centimeters);
- L is the distance between the impedance-measuring electrodes, in centimeters, measured on the patient; and
- Z is the impedance, in ohms, of the body section between the measuring electrodes, supplied by a plethysmograph or other such device, and which is a time variable signal usually consisting of both AC and DC components.

The values of E, k, $\mu$, s, and $\rho$ for any particular section of the body in a particular situation can be obtained from reference materials dealing with the mechanics of fluid flow through elastic tubes. See, for example, "Transport Phenomena in the Cardiovascular System" by Stanley Middleman, published by John Wiley & Sons of New York (1972). The value of L and $R_o$ may be measured with a scale on the patient, in centimeters.

When the above values for E, K, $\mu$, s, $R_o$, $\rho$, and L have been ascertained, the formula reduces to $$Q = (C/Z^4) \cdot (dz/dt) \qquad \text{(Formula No. 2)}$$

where C is a constant obtained by combining E, k, $\mu$, s, $R_o$ and $L^3$ in the relationship in which they appear in Formula No. 1 for the specific conditions of the test.

When the instantaneous rate of flow, Q, is known, the pulse or stroke volume V in cc may be expressed by the following equation:

$$V = \int_{\text{cycle}} Q \, dt \qquad \text{(Formula No. 3)}$$

the integration being over the period beginning at a point in one cycle to the corresponding point in the following cycle.

When the pulse or stroke volume V is known, the cardiac output, C.O., in cc per minute may be expressed as Formula:
$$C.O. = \int_0^{1\,min.} \int_{cycle} (Q\,dt)\,dt \quad \text{(Formula No. 4)}$$

Referring now to the drawing, the single FIGURE shown is a diagram illustrating my improved measuring system for determining, indicated and recording the values of Q, V and C.O. for a specific situation.

At the upper lefthand portion of this diagram the figure of a human is shown with two electrodes about his neck and two electrodes about his waist. Leads 10 and 11 are connected to the upper neck electrode and the lower waist electrode respectively. These are utilized to impress an alternating potential across the chest section. Leads 12 and 13 are connected respectively to the lower neck electrode and upper waist electrode; these are used to sense the impedance between the two electrodes.

The leads 10, 11, and 12, 13 are utilized in the plethysmograph 14 which may be the plethysmograph described by Kubicek et al or any other such device which will provide at its output a signal Z representative of impedance.

The signal Z as received from the plethysmograph is usually a combination of a direct current constant value and a variable portion. I can process the Z signal as it is, containing both the constant portion and the variable portion, or I may separate out the constant portion and process the variable portion, and may, if desired, again incorporate a constant to adjust the signal to a proper value at a later point in the system. In this description I use the character Z to represent the impedance whether or not the constant value has first been removed.

The impedance Z is then processed as will now be described. It may first be observed that two channels lead from the plethysmograph 14 to the multiplier 15. In the first of these channels, A, there is included, in series, the divider 16 and the multiplier 17, 18 and 19. In the second of these channels, B, there is included, in series, the differentiator 20 and the multiplier 24.

In channel A the signal Z is, in the embodiment illustrated, fed as one input to the divider 16. The other input is an adjustable constant $c$, which is the output from potentiometer 22 powered by source 23. The output from divider 16 is the signal $(c_1/Z)$.

The output $(c_1/Z)$ of divider 16 is fed as input into the stage 1 multiplier 17 which is designed to multiply the input by itself, or, in other words, the output is the square of the input, and may be designated $(c_2/Z^2)$, $c_2$ being a constant.

The output of multiplier 17 is fed as input to the multiplier 18 designed and connected to multiply the output of the multiplier 17 with Z, resulting in the output $(c_3/Z^3)$ where $c_3$ is a constant, and in turn the output $(c_3/Z^3)$ is fed as input to the multiplier 19 which is designed and connected to multiply its input $(c_3/Z^3)$ with Z resulting in the output $(c_4/Z^4)$ which is fed as input to the multiplier 15. The constants $c_2$, $c_3$ and $c_4$ are the result of the particular settings of the respective multipliers 17, 18 and 19.

In the diagram of the drawing the signal Z is shown being passed consecutively first through divider 16, then through multipliers 17, 18 and 19. It is necessary only that these units be in series and they need not be in this specific sequence. In other words, the divider may be aligned in the circuit subsequent to the multipliers as well as where it is shown in the diagram.

As to the multipliers 17, 18 and 19, it is understood that these may be made up of any number of units of selected types according to the power to which Z is to be raised and in accordance with the knowledge of the art. My invention contemplates the production of signals where Z is raised to the $n$ power, $n$ being 2 or more. Desirably $n$ may be 2 to 6 or 2 to 10, but preferably $n$ is 4. Most accurate results are obtained when Z is raised to the 4th power. When $n$ is other than 4, the resulting values will be exaggerated one way or the other. However, for some purposes of diagnosis, this exaggeration may be helpful. If it is desired that $n$ be 2, then multipliers 18 and 19 may be deleted. If desired that $n$ be 3, then multipliers 17 and 18 may be utilized and multiplier 19 deleted. If it is desired that $n$ be 4, then the multipliers may be used as illustrated, or two multipliers of the type which produce the square of the input would accomplish the same result. Any number or types of multipliers may be selected to provide the desired value of $n$ and with respect to channel A the term multiplier, multiplier device or multiplier means is understood to include one or more units of whatever character may be selected to produce a signal of the power indicated. These terms may embrace also devices which multiply the input by a factor of 2, 3, or the like to strengthen the signal or devices which both raise the input to a higher power and increase the signal by the incorporation of a factor.

In a modified form of the apparatus I may omit all multipliers in channel A, leaving only the divider 16 in this channel.

Turning now to the channel B, the impedance signal Z is fed as input to the differentiator 20 resulting in the output $(dz/dt)$ which, in the embodiment illustrated, is fed as input to the multiplier 24 at which a constant factor $a$ is incorporated, and the output of multiplier 24, a $(dz/dt)$, fed as a second input to multiplier 15. If the multiplier 24 is not needed to increase the strength of the signal or to incorporate a constant, this multiplier may be omitted and the signal fed directly to multiplier 15.

The multiplier 15 multiplies the signal $(c_4/Z^4)$ from channel A with the signal a $(dz/dt)$ from channel B resulting in the output $(b/Z^4) \cdot (dz/dt)$. This signal has a value the same as Formula No. 2 and represents the instantaneous rate of blood flow in cc per second. The signal from multiplier 15 is displayed on oscilloscope 35 and chart recorder 36.

The combined signal at the output of multiplier 15 may be fed to the integrator 25 which operates to integrate the signal over the pulse cycle resulting in the signal $$\int_{T_1}^{T_2} \frac{b}{Z^4} \cdot \frac{dz}{dt} \cdot dt$$

where $T_1$ and $T_2$ are corresponding points on successive cycles, and $b$ is a constant, which represents the stroke volume or the volume of the blood flowing in a pulse cycle in accordance with Formula No. 3.

The output signal of integrator 25 may be fed through the multiplier 26 where an adjustment factor to strengthen the signal or to add a constant may be incorporated. If not needed or necessary for the incorporation of this factor, multiplier 26 may be omitted. The signal whether or not it is passed through multiplier 26, may be fed to each of the recorder 27, the digital display 28 and the oscilloscope 29.

The signal from integrator 25, which represents the volume in cc, may be fed to a second integrator 30 for integrating the rate of flow signal over a selected period of time such as 1 minute. This signal, known as the cardiac output, C.O., represents the volume flow of blood in cc over a minute or whatever other period over which the last integration may be taken.

This signal, representing cardiac output, is fed to the recorder 32, and digital display 33, and the oscilloscope 34 for recording and visual representation.

The recorders 27, 32 and 36, the digital displays 28 and 33, and th oscilloscopes 29, 34 and 35, may each be called a display device or display means for indicating the values passed to it.

The signal at the output of the second integrator 30 may be described as $$\int_{T_3}^{T_4} \left( \int_{T_1}^{T_2} b_1 \cdot \frac{1}{Z^4} \cdot \frac{dz}{dt} \cdot dt \right) dt$$

where $T_3$ is the beginning of a selected time period and $T_4$ the end of the selected period, and $b_1$ is a constant.

As indicated earlier, the multiplier comprising units 17, 18, 19 are needed for raising the signal ($1/Z$) (or the signal Z if the divider comes after the multiplier) to the power $n$, but it is also contemplated that such units may operate to incorporate a factor to strengthen the signal in the event the signal may have become attenuated in the prior processing and/or to incorporate a constant.

The multipliers 24, 26 and 31 are mainly for the purpose of strengthening the signal at these points in the system in which case the multiplier is acting principally as an amplifier and may be simply amplifiers, or for adding a factor which is equivalent to all or a part of the value of the constants referred to in Formula No. 1. Where a multiplier unit is not needed for such purposes it may be omitted.

It is contemplated that all of the constants of Formula No. 1 which are common in uses to which the instrument will be put be built into the system where the apparatus is fabricated and assembled, and the remaining constants of Formula No. 1, which include L, and any other constants which depend on the specific situation of the test, be put into the system by adjustment of the multiplier units at the site of the test.

In the use of my improved system an operator may affix the electrodes about the neck and waist of the patient as indicated in the drawing diagram. If the test is to involve a leg or an arm or some other body section, then the electrodes would be affixed in a similar manner to such other body section. Then the instrument would be set for the particular situation of the test. If the test involves the chest section of a human, the multiplier units would be set to incorporate, for example, the modulus of elasticity E and the constants $k$ and $R_o$ and the constant L (other specific constants such as $\mu$ and $p$ may already have been built into the system).

Suitably the display devices, or at least the oscilloscope and digital display which are visual, may be located so that the surgeon or physician may have only to look up at these displays to get at a glance the information about blood flow characteristics.

Normally the apparatus will be set so that the signal Z is raised to the power 4 this being the most accurate setting in terms of familiar units of measurement but when, for example, the physician may wish to emphasize the showing of some small variation the system may be adjusted to include a different or additional unit in the multiplier assembly, 17, 18, 19 to make the value of $n$ greater, such as 6, 8, 10 or 100, which makes some characteristics show up in magnified form on the display device.

The integrator 25 operates in accordance with suitable reset signal, integrate signal, and stop integration and hold signal, each signal coming into the integrator 25 either from a suitable manual device or a suitable point in the diagram shown in the drawing, or from some external clock or other such device.

Normally the integrator 25 would be set to start the integration at the minimum value of the cycle and end when the value is again a minimum or begin when the value is maximum and end when again it comes to a maximum, the beginning being at a point of one cycle and ending at the corresponding point of the succeeding cycle. An alternative which would give the same result would be to begin at a minimum value and end at a maximum value and incorporate a suitable factor. The setting on the integrator is accomplished in ways known to the art by operating the stop, hold and reset signals at the integrator.

I believe that the system for display of information about blood flow characteristics described herein is of greater usefulness than any such system heretofore available because of its accuracy and because the information is made available as the blood flow events occur and without delay or need for calculation.

While I have described my invention in connection with a specific embodiment with mention of certain variations, it will be understood that many changes and variations are possible and many modifications of the method and apparatus may be made all within the spirit of the invention and the scope of the claims.

What is claimed is:
1. In a method for noninvasively measuring rate of blood flow in a section of a living body, the steps of
    passing a signal Z representing impedance of said section through a first channel which includes, in series, a divider device and a multiplier device to obtain a signal ($c_4/Z^n$) where $c_4$ is a constant and $n$ is a value of 2 or more,
    passing said signal Z through a second channel which includes a differentiator to obtain the signal a ($dz/dt$) where $a$ is a constant and multiplying said signals ($c_4/Z^n$) and a ($dz/dt$) in a multiplier to obtain the resulting signal ($b/Z^n$) · ($dz/dt$) where $b$ is a constant and where the resulting signal represents the instantaneous rate of flow of blood in said body section.

2. A method as set forth in claim 1 in which $n$ is a value from 2 to 10.

3. A method as set forth in claim 1 in which $n$ is 4.

4. A method as set forth in claim 1 including the added step of passing said signal $(b/Z^n) \cdot (dz/dt)$ through an integrator to obtan the resulting signal $$\int_{T_1}^{T_2} b \cdot \frac{1}{Z^n} \cdot \frac{dz}{dt} \cdot dt$$

where $T_1$ and $T_2$ are points of time in a cardiac cycle, $b$ is a constant, and where said resulting signal represents the volume flow of blood in said section in the time period between said points.

5. A method as set forth in claim 4 wherein said points of time are corresponding points on two successive cardiac cycles, whereby said resulting signal represents the volume flow of blood in said section during one complete cycle.

6. A method as set forth in claim 5 including the step of passing said signal $$\int_{T_1}^{T_2} b \cdot \frac{1}{Z^n} \cdot \frac{dz}{dt} \cdot dt$$

into a second integrator to obtain the resulting signal $$\int_{T_3}^{T_4} \left( \int_{T_1}^{T_2} b \cdot \frac{1}{Z^n} \cdot \frac{dz}{dt} \cdot dt \right) dt$$

in which $T_3$ and $T_4$ are the limits of a selected time period, $b$ is a constant, and said last mentioned resulting signal represents the volume flow of blood in said section during said selected period.

7. A method as set forth in claim 6 including passing said signal $$\int_{T_3}^{T_4} \left( \int_{T_1}^{T_2} b \cdot \frac{1}{Z^n} \cdot \frac{dz}{dt} \cdot dt \right) dt$$

to a display device whereby there is indicated at said device the volume of blood flow over said selected time period.

8. A method as set forth in claim 7 in which said volume signal $$\int_{T_3}^{T_4} \left( \int_{T_1}^{T_2} b \cdot \frac{1}{Z^n} \cdot \frac{dz}{dt} \cdot dt \right) dt$$

is passed through a multiplier to incorporate a factor into said volume signal after it has left said second integrator and before it is passed to said display device to produce the signal $$\int_{T_3}^{T_4} \left( \int_{T_1}^{T_2} b_1 \cdot \frac{1}{Z^n} \cdot \frac{dz}{dt} \cdot dt \right) dt$$

9. A method as set forth in claim 4 including the step of passing said signal $$\int_{T_1}^{T_2} b \cdot \frac{1}{Z^n} \cdot \frac{dz}{dt} \cdot dt$$

to a display device whereby there is indicated at said device the volume of blood flow between said points of time.

10. A method as set forth in claim 9 in which said volume flow of blood signal $$\int_{T_1}^{T_2} b \cdot \frac{1}{Z^n} \cdot \frac{dz}{dt} \cdot dt$$

is passed through a multiplier to incorporate a factor into said volume flow of blood signal after said volume flow of blood signal has left said integrator and before it is passed to said display device to produce the signal $$\int_{T_1}^{T_2} b_1 \cdot \frac{1}{Z^n} \cdot \frac{dz}{dt} \cdot dt$$

where $b_1$ is a constant.

11. In the method set forth in claim 1 the step of incorporating into the system a value for the constant $b$ which is equivalent to $$\frac{0.5}{16\pi^2} \cdot \frac{E(k^2-1)}{\mu s R_o} \cdot \rho^3 L^3$$

where
E is the average modulus of elasticity of the arterial walls;
$k$ is the average ratio of outer to inner radii of the arterial walls;
$\mu$ is the viscosity of blood;
$s$ is the average speed of propagation of pressure through the arterial walls;
$R_o$ is the average radius of the chest of the patient being tested;
$p$ is the electrical resistivity of blood; and
L is the distance between the points on the body section between which the impedance is taken.

12. In apparatus for determining the instantaneous blood flow in a section of a living body, a channel which includes, in series, divider means for converting its input to an inverse value and multiplier means for raising its input to an exponential power of 2 or more, a second channel which includes a differentiator, means for delivering to one end of each of said channels a signal representative of the impedance of said body section, and means for multiplying signal at the other end of said first-mentioned channel with the signal at the other end of said second channel to produce a signal at its output which is representative of the instantaneous rate of flow of blood in said body section.

13. Apparatus as set forth in claim 12 in which said exponential power is from 2 to 10.

14. Apparatus as set forth in claim 13 in which said exponential power is 4.

15. Apparatus as set forth in claim 12 including integrator means having its input connected with the output of said last mentioned multiplier means for integrating said signal which is representative of flow rate, over a whole cardiac cycle or part thereof whereby there is obtained at the output of said integrator means a signal representing stroke volume.

16. Apparatus as set forth in claim 15 including a display means connected with said integrator means for indicating the stroke volume.

17. Apparatus as set forth in claim 16 including multiplier means connected between said integrator means and said display means for incorporating a factor into a signal passed therethrough.

18. Apparatus as set forth in claim 15 including second integrator means connected with the output of said first mentioned integrator means for integrating the value of said stroke volume over a selected period of time.

19. Apparatus as set forth in claim 18 including a second display means connected to the output of said second integrator means for indicating the value of blood flow over said selected period of time.

20. Apparatus as set forth in claim 19 including multiplier means connected between said second integrating means and said second display means for incorporating a factor into a signal passed therethrough.

21. Apparatus as set forth in claim 12 in which said second channel includes adjusting multiplier means for incorporating a factor into a signal passed therethrough.

* * * * *